United States Patent
Roby et al.

(10) Patent No.: US 10,881,514 B2
(45) Date of Patent: Jan. 5, 2021

(54) IMPLANT ASSEMBLY TOOLS AND METHODS

(71) Applicant: Biomet Manufacturing, LLC, Warsaw, IN (US)

(72) Inventors: Keith A. Roby, Jersey City, NJ (US); John Chernosky, Brick, NJ (US); Joseph Markham, Hillsborough, NJ (US); Robert G. Deluca, Bethlehem, PA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 316 days.

(21) Appl. No.: 15/976,243

(22) Filed: May 10, 2018

(65) Prior Publication Data
US 2018/0333263 A1 Nov. 22, 2018

Related U.S. Application Data

(60) Provisional application No. 62/508,489, filed on May 19, 2017.

(51) Int. Cl.
*A61F 2/30* (2006.01)
*A61B 17/17* (2006.01)
(Continued)

(52) U.S. Cl.
CPC ...... *A61F 2/30734* (2013.01); *A61B 17/1778* (2016.11); *A61F 2/4081* (2013.01);
(Continued)

(58) Field of Classification Search
CPC ............. A61B 17/1778; A61B 17/1684; A61F 2/30734; A61F 2/4081; A61F 2/4637;
(Continued)

(56) References Cited

U.S. PATENT DOCUMENTS 9,861,376 B2 * 1/2018 Chavarria .......... A61B 17/1659
606/80
9,955,984 B2 * 5/2018 Winslow ................ A61B 17/17
606/79

(Continued)

FOREIGN PATENT DOCUMENTS

WO 2013086440 6/2013
WO 2018213094 11/2018

OTHER PUBLICATIONS

"International Application Serial No. PCT US2018 032036, International Search Report dated Aug. 27, 2018", 6 pgs.
(Continued)

*Primary Examiner* — Jessica Weiss
(74) *Attorney, Agent, or Firm* — Schwegman Lundberg & Woessner, P.A.

(57) ABSTRACT

Various implant systems and methods of implantation are disclosed herein. The systems and methods allow a surgeon to accurately determine a suitable fastener trajectory for attaching certain components of the implant system to bone. In this manner, an appropriate fastener trajectory can be selected and used during a surgical procedure to ensure better purchase and attachment of the various components of the implant system to the bone.

10 Claims, 12 Drawing Sheets

(51) Int. Cl.
*A61B 17/58* (2006.01)
*A61B 17/88* (2006.01)
*A61F 2/40* (2006.01)
*A61F 2/46* (2006.01)
*A61B 17/16* (2006.01)

(52) U.S. Cl.
CPC .......... *A61F 2/4637* (2013.01); *A61F 2/4684* (2013.01); *A61B 17/1684* (2013.01); *A61F 2/30767* (2013.01); *A61F 2/4603* (2013.01); *A61F 2002/30332* (2013.01); *A61F 2002/30367* (2013.01); *A61F 2002/30604* (2013.01); *A61F 2002/30736* (2013.01); *A61F 2002/4085* (2013.01); *A61F 2002/4627* (2013.01)

(58) Field of Classification Search
CPC .. A61F 2/4684; A61F 2/4603; A61F 2/30767; A61F 2002/30736; A61F 2002/4085; A61F 2002/30604; A61F 2002/4627
USPC ............ 606/79–85, 96–98; 623/19.11–19.12
See application file for complete search history.

(56) References Cited

U.S. PATENT DOCUMENTS

| | | | | |
|---|---|---|---|---|
| 10,441,298 B2* | 10/2019 | Eash | .................. | A61B 17/1778 606/80 |
| 2006/0276796 A1* | 12/2006 | Creger | ............... | A61B 17/1767 606/79 |
| 2012/0239042 A1* | 9/2012 | Lappin | ............... | A61B 17/1778 606/80 |
| 2012/0239043 A1* | 9/2012 | Lappin | ............... | A61B 17/1778 606/80 |
| 2012/0239051 A1* | 9/2012 | De Wilde | .......... | A61B 17/1778 606/96 |
| 2012/0239156 A1* | 9/2012 | De Wilde | .......... | A61F 2/30771 623/19.11 |
| 2013/0110116 A1* | 5/2013 | Kehres | ............... | A61B 17/1739 606/96 |
| 2014/0046383 A1* | 2/2014 | Asfora | ............... | A61B 17/8811 606/304 |
| 2015/0073424 A1* | 3/2015 | Couture | ............. | A61B 17/1778 606/96 |
| 2016/0030196 A1* | 2/2016 | Eraly | ................. | A61B 17/1739 606/96 |

OTHER PUBLICATIONS

"International Application Serial No. PCT US2018 032036, Written Opinion dated Aug. 27, 2018", 7 pgs.

"International Application Serial No. PCT US2018 032036, International Preliminary Report on Patentability dated Nov. 28, 2019", 9 pages.

"European Application Serial No. 18727604.3, Response to Communication pursuant to 161(1) and 162 EPC filed Jul. 27, 2020", 11 pgs.

* cited by examiner

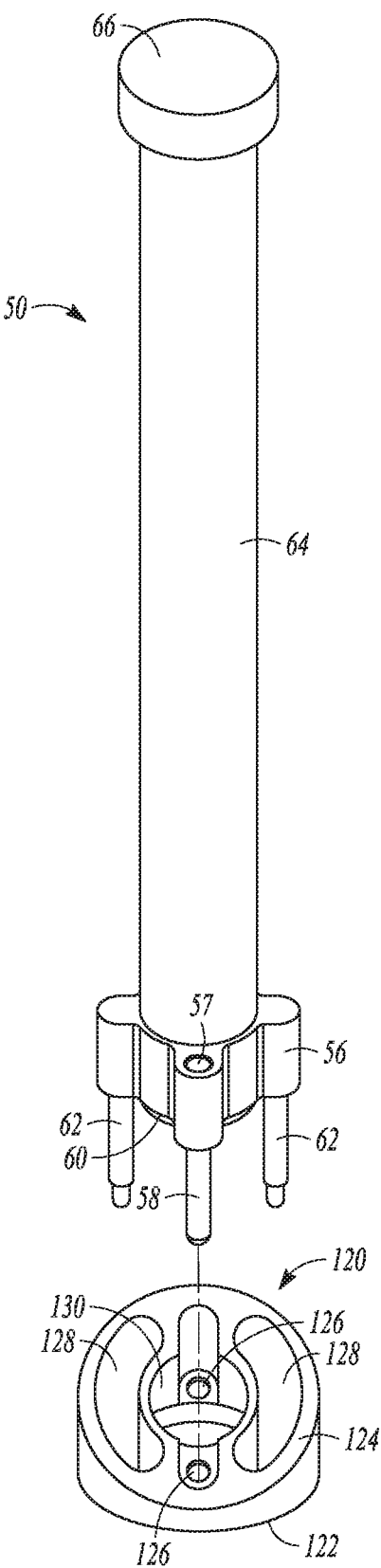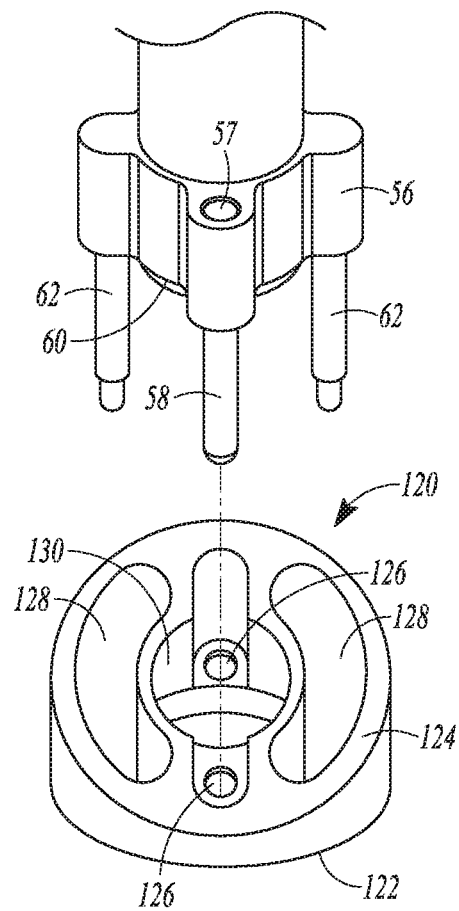
FIG. 5B
FIG. 5A

IMPLANT ASSEMBLY TOOLS AND METHODS

PRIORITY APPLICATIONS

This application claims the benefit of priority to U.S. Provisional Application Ser. No. 62/508,489, filed May 19, 2017, the content of which is incorporated herein by reference in its entirety.

FIELD OF THE DISCLOSURE

The present disclosure relates to tools and methods for implanting implants into the body of a patient, in particular shoulder (e.g., glenoid) implants and their components.

BACKGROUND

Shoulder replacement surgery, particularly reverse total shoulder arthroplasty (rTSA), can involve implanting a glenosphere on a patient's glenoid and/or a humeral stem into the humerus. The humeral stem can have a bearing that interacts with the glenosphere to restore normal shoulder function. In some cases, a baseplate can be attached to the patient's glenoid, and the baseplate can engage with the glenosphere to secure the glenosphere relative to the glenoid.

In some rTSA procedures, a patient's glenoid may also have a defect that requires eccentric reaming or some other suitable preparation of the glenoid for the correction of the defect. This can result in a situation in which a certain portion of the patient's glenoid has more bone removed relative to other portions of the glenoid. In such cases, an augment might be used with a baseplate to ensure proper support of the baseplate by the patient's bone. Likewise, one (1) or more screws might extend through the baseplate and/or the augment to secure both components to the glenoid.

In attaching components to bone during a rTSA, a surgeon must select an appropriate screw trajectory or a screw starting point for securing the particular component(s) to the bone. Certain screw trajectories or starting points may be more clinically desirable than others due to improved bone quality, or several other factors. Yet, it is difficult for a surgeon to select a particular trajectory or screw starting point, and then attach the relevant component(s) to the bone (e.g., glenoid) using that trajectory or point. For instance, a surgeon may make an error or otherwise select a non-optimal screw trajectory or starting point for attaching a component like a baseplate and/or an augment to a patient's glenoid, which can result in the screw failing to purchase securely in the patient's bone. This could result in the baseplate and/or augment loosening over time and, ultimately, failing.

It is therefore an object of the present disclosure to provide tools, implants, and methods to enable surgeons to select appropriate screw trajectories and/or starting points and attach implant components to a patient using such trajectories and/or starting points in a manner that improves patient outcomes.

SUMMARY

To better illustrate the system disclosed herein, a non-limiting list of examples is provided here:

Example 1 includes an implant comprising a tool having a shaft and a first projection, a baseplate having a post and a first fastener aperture, and an augment having a first opening configured to lockingly receive the post, wherein the first projection of the tool is insertable into the first fastener aperture of the baseplate and, when the first projection of the tool is inserted into the first fastener aperture, the first projection acts as a guide that directs the post of the baseplate into the first opening of the augment along a pre-defined trajectory.

Example 2 includes a method of selecting and establishing a fastener starting point for an implant system comprising inserting a first projection of a tool into a first fastener aperture of a baseplate, moving the baseplate towards an augment with the first projection of the tool extending through the first fastener aperture of the baseplate, such that a post of the baseplate is received in an opening of the augment, the first projection acting as a guide that guides the post of the baseplate into the opening of the augment, and locking the post of the baseplate within the opening of the augment so that an axis of the first fastener aperture of the baseplate is configured to establish a first fastener starting point when a first fastener is inserted through the first fastener aperture of the baseplate.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein:

FIG. 5A is a perspective view of the translator tool of FIGS. 2-3 being engaged with an augment, FIG. 5B is a close-up view of FIG. 5A.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

Figure 1A:
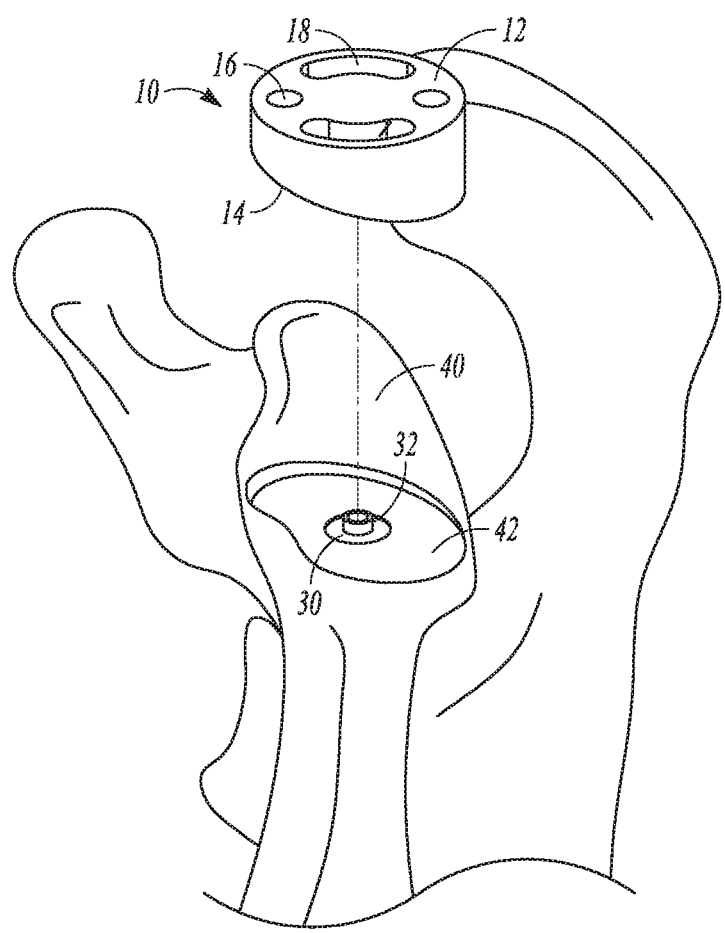
FIG. 1A is a perspective view of a provisional augment being attached to a patient's glenoid.

In describing the examples of the disclosure illustrated and to be described with respect to the drawings, specific terminology will be used for the sake of clarity. However, the disclosure is not intended to be limited to any specific terms used herein, and it is to be understood that each specific term includes all technical equivalents.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves. In addition, the terms implant and prosthesis, and variations thereof, can be used interchangeably.

The present disclosure is directed to surgical tools, implants, and methods for selecting an effective screw trajectory and/or screw starting point for a baseplate and/or augment used in a shoulder replacement procedure (e.g., a rTSA), and attaching such components to a patient's glenoid during the procedure. In an example, the rTSA of the present disclosure can utilize a translator tool 50 and provisional augment 10 to select an appropriate screw trajectory and/or screw starting point (FIGS. 1A-3), then translator tool 50 can be used to attach a baseplate 80 to an augment 120 so that the selected screw trajectory is maintained and/or that screws are inserted starting at the screw starting point. Augment 120 and baseplate 100 can then be attached to the patient's glenoid, whereafter further components needed for the rTSA can be attached to baseplate 100 (e.g., a glenosphere).

Figure 1B:
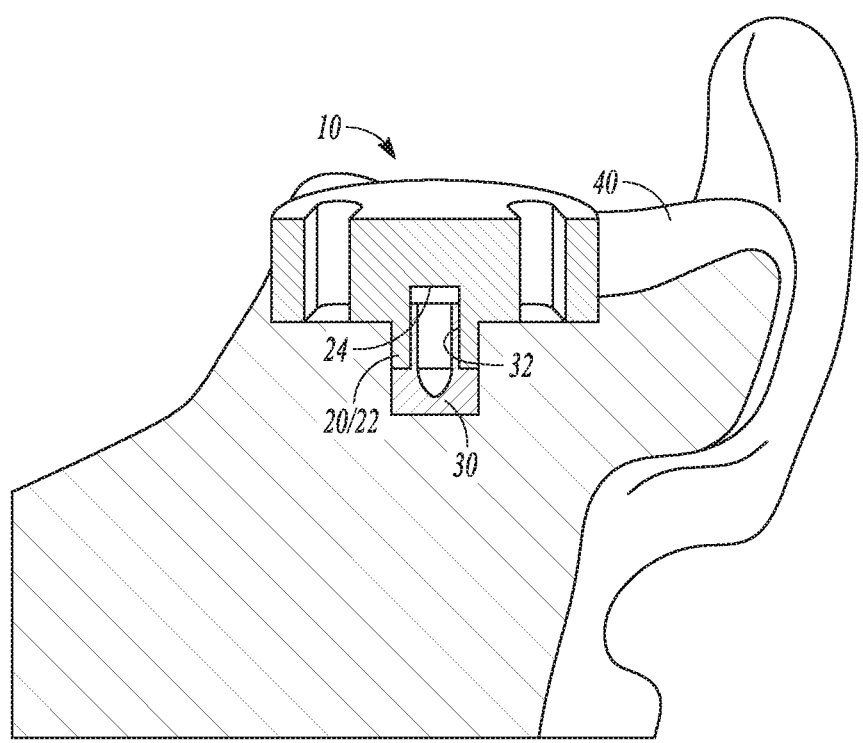
FIG. 1B is a cross-sectional view of the provisional augment of FIG. 1A attached to the patient's glenoid.
Figure 1C:
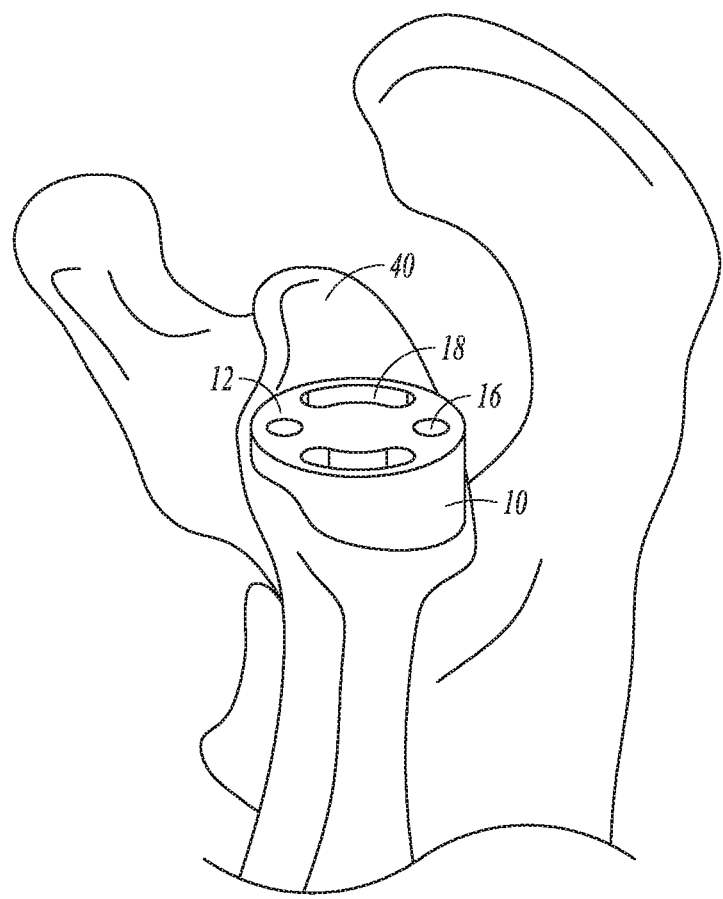
FIG. 1C is a perspective inferior view thereof.

Referring to FIGS. 1A-C, a provisional augment 10 is shown as being attached to a patient's glenoid 40. Provisional augment 10 can have top and bottom surfaces 12, 14 and, in an example, bottom surface 14 can be angled relative to top surface 12. Provisional augment 10 can have a substantially cylindrical, polygonal prism, or truncated conical body, a first set of holes 16 through the body, and a second set of holes 18 through the body. In an example, holes 16 can be substantially circular in shape, while holes 18 can form elongate slots. Further, slots 18 can be curved along their length. Both sets of holes 16, 18 can extend entirely through provisional augment 10, such that holes 16, 18 are exposed at both top and bottom surfaces 12, 14. Provisional augment 10 can also have a projection 20 extending from its bottom surface 14, which in an example can include a cavity 24 and one (1) or more tabs 22 (FIG. 1B).

As shown in FIGS. 1B-C, provisional augment 10 can be attached to a reamed portion 42 of a patient's glenoid 40. In an example, an insert or bushing 30, optionally threaded, can be inserted into a bore formed in the patient's glenoid 40, and provisional augment 10 can attach to insert 30. For instance, provisional augment 10 can attach to insert 30 by inserting its projection 20 over a projection 32 of insert 30. Projection 32 of insert 30 can be received within cavity 24 of projection 20 of provisional augment 10 and, in an example, tabs 22 of projection 20 can engage with similarly-shaped slots (not shown) on insert 30. In alternative examples, projection 32 of insert 30 can be received within cavity 24 of projection 20 of provisional augment 10 by way of a press-fit connection, a threaded connection, or a slip-fit (loose) connection. Further, the interaction between tabs 22 of projection 20 and the slots (not shown) on insert 30 can act to rotationally constrain or lock provisional augment 10 relative to insert 30.

In another example, provisional augment 10 can be composed of a translucent material so that a surgeon can confirm that provisional augment 10 is properly seated on the patient's glenoid 40.

Figure 2:
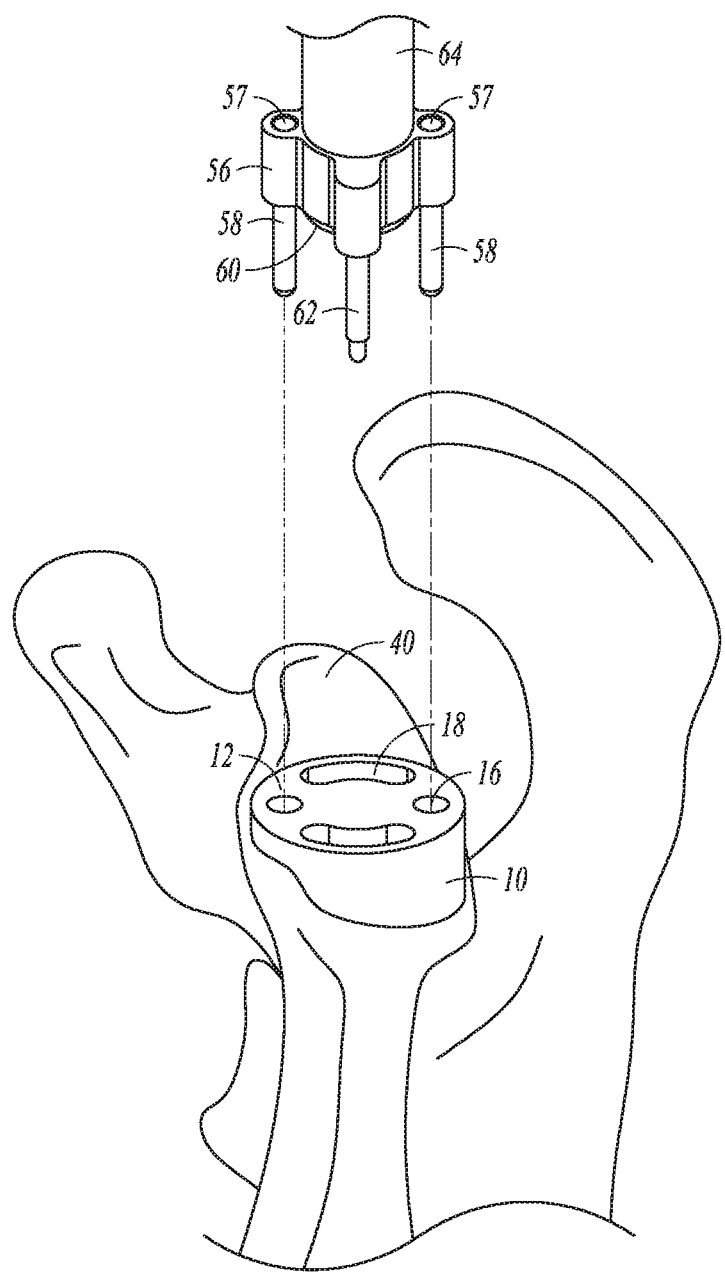
FIG. 2 is a close-up perspective view of a translator tool of the present disclosure being attached to the provisional augment of FIGS. 1A-C.
Figure 3:
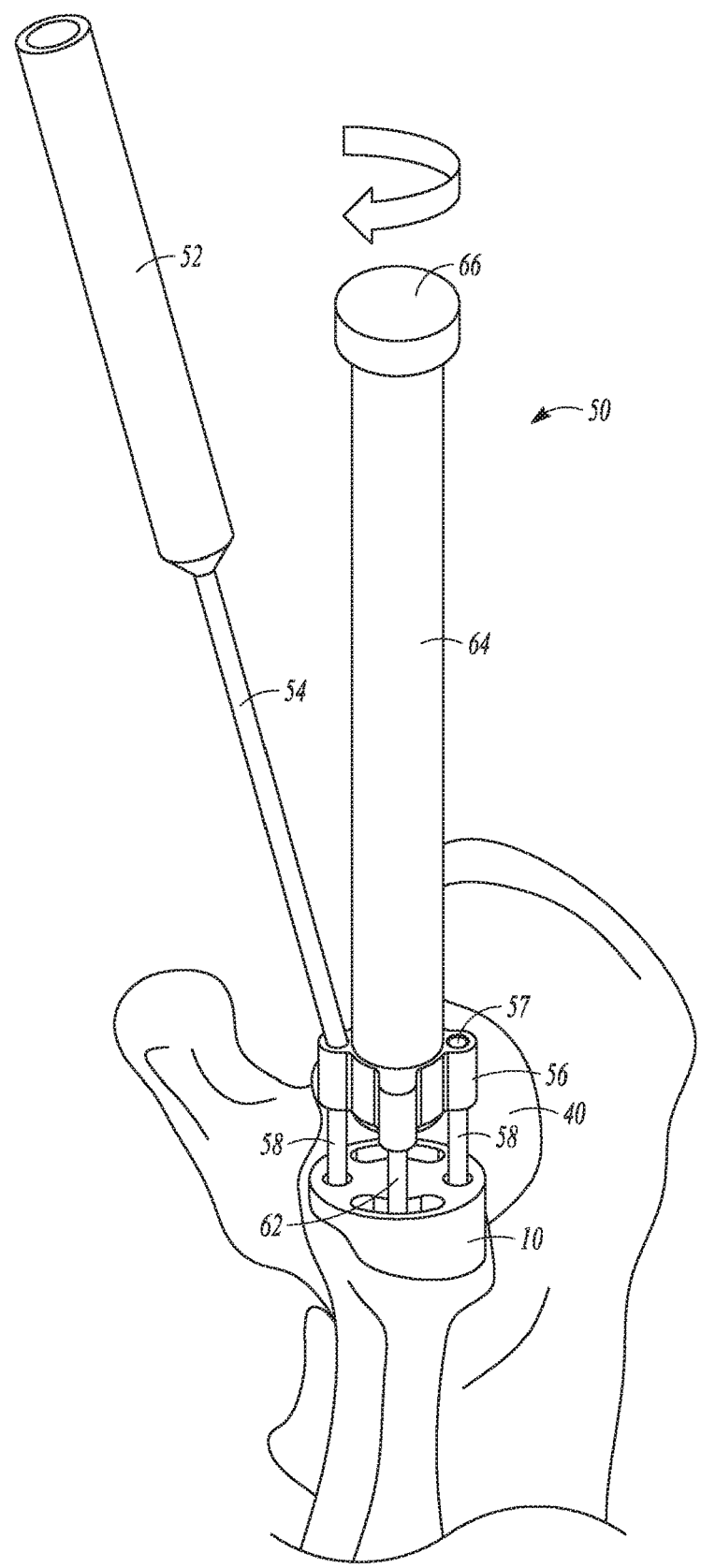
FIG. 3 is a perspective view of FIG. 2 showing the entire translator tool and its handle.
Figure 7:
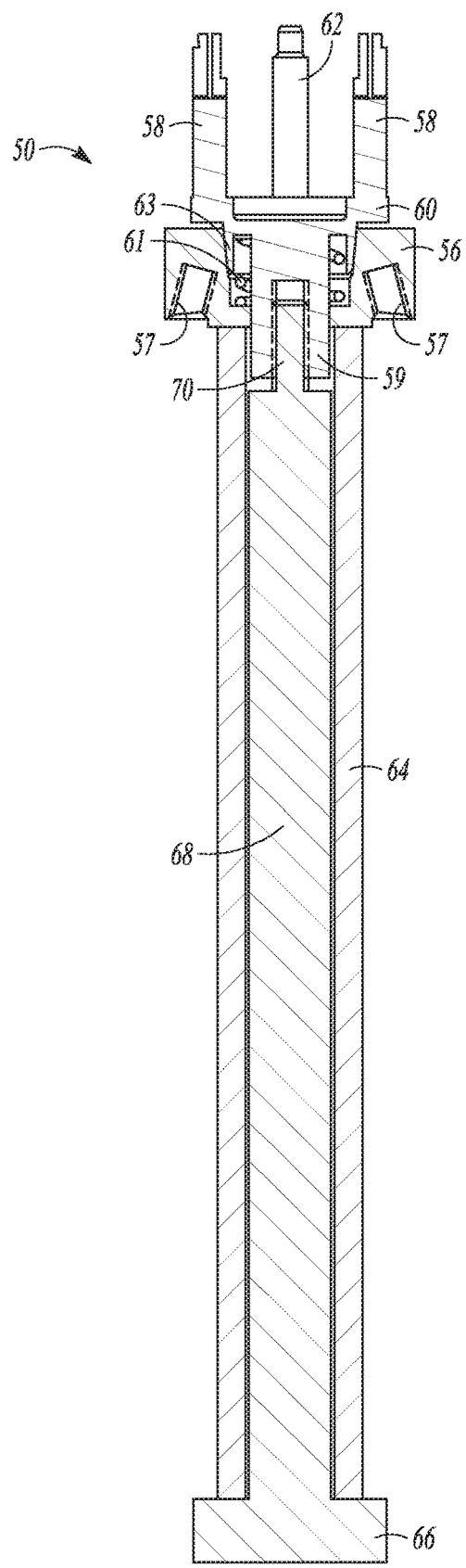
FIG. 7 is a cross-sectional view of the translator tool of the above-mentioned figures.

FIGS. 2-3 and 7 depict a translator tool 50 that can be used to determine and set a screw trajectory and/or screw starting point for fixing an augment and/or baseplate to glenoid 40. As shown, translator tool 50 can include a shaft 64, a knob 66, and a head 56. Further, a handle 52 having a shaft 54 can be attached to head 56 for manipulating head 56 (FIG. 3), as described in more detail below.

Referring to FIG. 7, translator tool 50's head 56 can have one (1) or more pins 58 extending downwards relative to head 56, which in an example can be attached to a body 60 of translator tool 50. Indeed, in an example, body 60 can have pins 58 attached thereto, and a projection 63 extending from body 60 that can be received in a cavity of head 56. The cavity of head 56 can be tapered, and projection 63 can likewise be tapered, as shown in FIG. 7. Further, another projection 59 can extend from body 60, and, in an example, projection 59 can include a bore (e.g., a threaded bore). A spring 61 can be arranged around projection 59, and can be disposed in a groove formed between projections 59, 63, as illustrated in FIG. 7. Spring 61 can be a helical spring that is predisposed to force body 60 away from head 56. In an example, translator tool 50 can also include a knob 66 that can have a shaft 68 with a projection 70, which can be sized to fit within the cavity of projection 59, as shown in FIG. 7. Projection 70 can be threaded to threadably engage with the threaded cavity of projection 59. Such interaction can assist with fixing body 60 and/or head 56 relative to shaft 64 of translator tool 50. As detailed below, pins 58 attached to body 60 can be movable when body 60 is in an unlocked position, but can be fixed or otherwise non-movable once body 60 is locked in position. Such locking and unlocking can occur when knob 66 and its shaft 68 are rotated.

Head 56 of translator tool 50 can include one (1) or more additional pins 62 that, in example, are engaged to head 56. For instance, pins 62 can be integral or directly attached to head 56. Head 56 can also, in an unlocked orientation, rotate relative to shaft 64 and/or pins 58 of translator tool 50. For instance, a handle 52 can be attached to head 56 and/or translator tool 50 via a shaft 54 (FIG. 3), which, upon manipulation by a user, can act to rotate head 56 of translator tool 50 relative to shaft 64. In an example, handle 52 can be grasped by a user and manipulated to rotate head 56 and pins 62 about a longitudinal axis extending through shaft 64. In this way, pins 62 can be moved about the longitudinal axis to different positions for reasons discussed in more detail below. In a further example, shaft 54 of handle 52 can be attached to head 56 of translator tool 50 in a removable manner, such as by threading, press-fitting, or otherwise removably connecting shaft 54 to a portion of head 56. In a particular example, a distal end section of shaft 54 is threaded and head 56 includes one (1) or more threaded openings 57 that can threadably receive shaft 54, as shown in FIG. 7.

Translator tool 50 can also include a knob 66 that, when rotated in a first direction, acts to lock head 56 and/or body 60 about the longitudinal axis of shaft 64 of translator tool 50. Further, when knob 66 is rotated in a second direction opposite the first direction, head 56 and/or body 60 can become unlocked about the longitudinal axis of shaft 64 so that head 56 and/or body 60 can be rotated about the longitudinal axis, as described above. The mechanism permitting such locking and locking can include projection 70 of shaft 68 of knob 66 interacting with the cavity of projection 59 of body 60. In short, when knob 66 is rotated, its projection 70 can thread into the threaded cavity of projection 59 of body 60, causing body 60 to move towards knob 66. As body 60 moves towards knob 66, tapered projection 63 can be pulled further into the tapered cavity of head 56 against the force of spring 61. This can cause head 56 to become wedged or compressed between body 60 and shaft 64 of translator tool 50, as shown in FIG. 7, which can lock head 56 about the longitudinal axis of shaft 64. In addition, as tapered projection 63 is pulled into the tapered cavity of head 56 against spring 61, tapered projection 63 can become press-fit within the tapered cavity due to the interaction between the tapers, which can act to lock body 60 about the longitudinal axis of shaft 64. Alternatively, body 60 can become locked simply due to the friction between body 60 and head 56 when head 56 is compressed between body 60 and shaft 64. Thus, both sets of pins 58, 62 can move when head 56 and body 60 are unlocked, and can be fixed in position when head 56 and body 60 are locked, as described above.

As shown in FIGS. 2-3, translator tool 50 can be attached to provisional augment 10 via pins 58, 62. In particular, pins 58 of translator tool 50 can be inserted into holes 16 of provisional augment 10 (optionally circular), and pins 62 can be inserted into holes 18 (optionally slots). As described in connection with the surgical method below, pins 62 can be moved along the length of slots 18 in either direction by way of rotation of head 56 about the longitudinal axis of shaft 64 of translator tool 50. After rotation, head 56 and pins 62 can be locked rotationally relative to shaft 64 by rotating knob 66 into a locked orientation. Pins 62 can therefore be moved within slots 18 and then locked at a position selected by the surgeon, which establishes a desired screw trajectory and/or screw starting point to be used later in attaching an augment and/or a baseplate to a glenoid surface (e.g., augment 120 and/or baseplate 80 to glenoid 40). In addition, during rotation of head 56, pins 58 and/or their associated body 60 can remain fixed in location about the longitudinal axis of shaft 64 of translator tool 50 by virtue of pins 58 being inserted into holes 16. For instance, pins 58 and holes 16 can have substantially the same diameter so that pins 58 are relatively immovable laterally within holes 16. Thus, pins 58 can be somewhat fixed laterally inside holes 16 while head 56 and pins 62 can rotate.

Figure 4A:
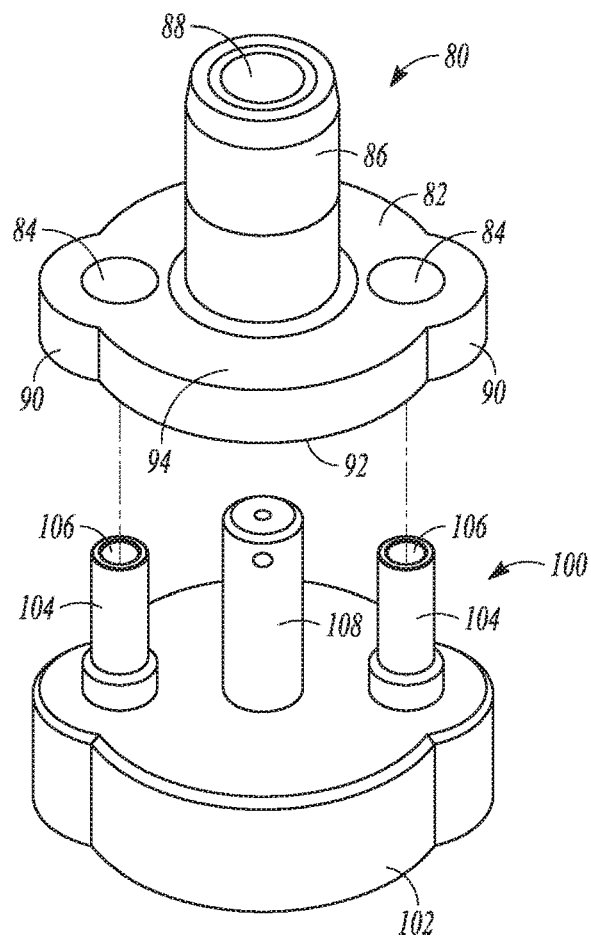
FIG. 4A is a perspective view of a baseplate being attached to an alignment guide.
Figure 4B:
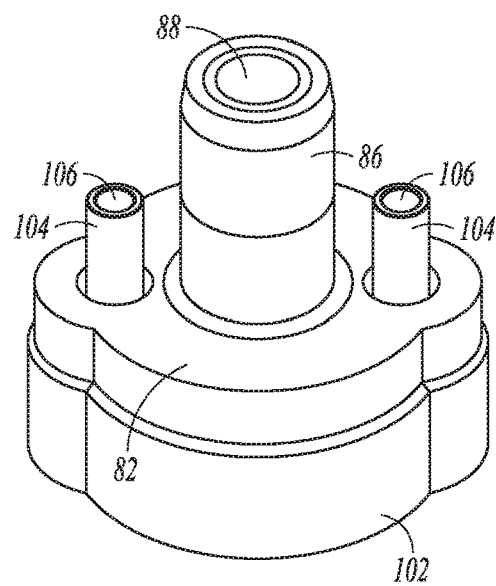
FIG. 4B is a perspective view showing the baseplate fully connected to the alignment guide.

Referring to FIGS. 4A-B, a baseplate 80 and an alignment guide 100 are shown. Baseplate 80 can be used in rTSA procedures to connect to other components, such as a glenosphere (not shown). Baseplate 80 can include a body 82 with one (1) or more holes 84, for example for receiving bone screws to connect baseplate 80 to bone (e.g., glenoid 40). Body 82 can include top and bottom surfaces 92, 94 and holes 84 can extend through body 82 and be exposed to top and bottom surfaces 92, 94. A post 86 can also extend downwardly from body 82 and can include a bore 88 defined by post 86. In an example, post 86 can be tapered (e.g., a Morse taper). In a further example, the taper of post 86 can permit engagement of baseplate 80 with another component in a locking, morse-tapered arrangement. Baseplate 80 can also include tabs 90 on either side of body 82, and body 82 can be roughly elliptical in shape.

Alignment guide 100 can be used as a guide to ensure that baseplate 80 connects to augment 120 properly so that the axes of holes 84 of baseplate 80 extend along the proper screw trajectory and/or screw starting point selected by the surgeon. Alignment guide 100 can have a body 102 that can be similar in shape to body 82 of baseplate 80. A set of posts 104 can extend from body 102. Posts 104 can include a bore 106 through each post 104, which optionally can extend through body 102 as well. In addition, alignment guide 100 can include a center post 108 extending from body 102 for insertion into post 86 of baseplate 80. In an example, center post 108 can be tapered or non-tapered.

Figure 5C:
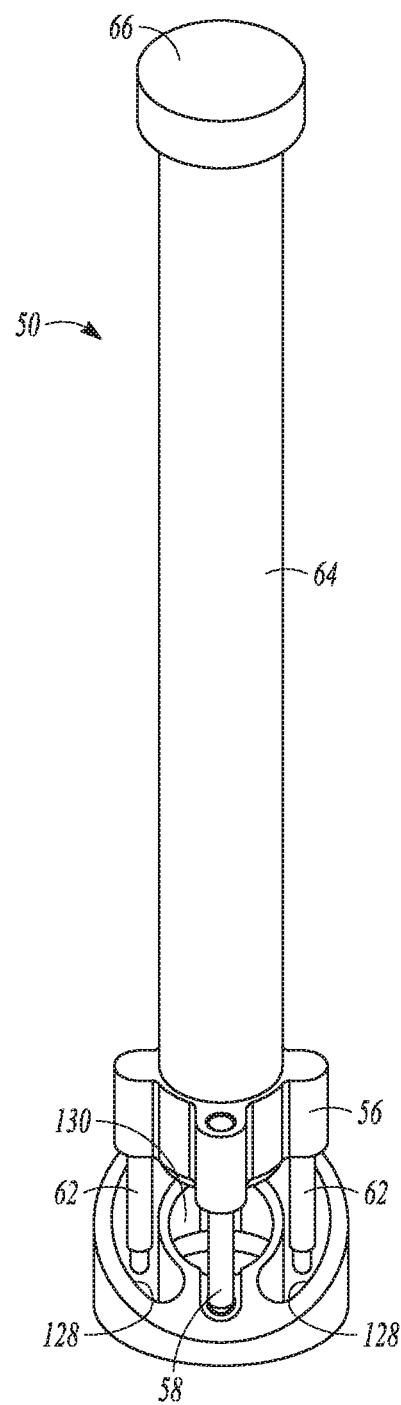
FIG. 5C is a perspective view of the translator tool of FIGS. 2-3 fully connected to the augment.

FIGS. 5A-C depict translator tool 50 and an augment 120. Augment 120 can include top and bottom surfaces 122, 124, and bottom surface 124 can be angled relative to top surface 122. Further, augment 120 can have holes 126 that can be sized to receive pins 58 of translator tool 50, and holes 128 that can be sized to receive pins 62 of translator tool 50. In an example, holes 126 can be substantially circular in shape, and holes 128 can be formed as elongate slots. Elongate slots 128 can also be curved along their length, as shown. In addition, holes 126, 128 can extend entirely through augment 120 so that holes 126, 128 are exposed on top and bottom surfaces 122, 124 of augment 120.

The present disclosure contemplates that a kit of components (not shown) can be provided for use by a surgeon. For instance, a kit of provisional augments 10 and augments 120 can be provided, where the kit can have augments 10, 120 of different thicknesses and/or also different angulations between top and bottom surfaces 12, 14 of provisional augment 10 and top and bottom surfaces 122, 124 of augment 120. Indeed, in an example, certain augments 10, 120 in the kit can have an angulation between top and bottom surfaces 12, 14, 122, 124 of anywhere between about 5-60°. Further, the clocking of holes 16 and slots 18 of provisional augment 10 and holes 126 and slots 128 of augment 120 can be changed or be different for different provisional augments 10 and/or augments 120 within a kit. For example, taking the orientation of holes 16 and slots 18 of provisional augment 10 as a zero-degree baseline, holes 16 and slots 18 can be repositioned (e.g., rotated clockwise) at any degree between about 0-360°. In other words, holes 16 and slots 18 of provisional augment 10 can be repositioned clockwise relative to their orientation in the current figures (e.g., FIG. 1A). The same is true of holes 126 and slots 128 of augment 120 e.g., such holes 126 and slots 128 can be repositioned clockwise relative to their orientation in the current figures (e.g., FIGS. 5A-B) by anywhere between 0-360°. This can create a situation in which a kit of provisional augments 10 and augments 120 are provided with holes 16, 126 and slots 18, 128 of different clocking. In addition, as set forth above, certain provisional augments and/or augments 120 within the kit can have different angulations top and bottom surfaces 12, 14 of provisional augment 10 and top and bottom surfaces 122, 124 of augment 120. Such a kit can therefore encompass the different hole and slot positions that might be required for a particular patient, in addition to different angulations for the provisional augment and/or the augment that are needed.

An exemplary method of using the above-described components will now be described. It is to be understood that the order of steps of the method can be changed, and that different surgical steps can be used to achieve the objectives of the disclosure.

First, as shown in FIGS. 1A-C, a surgeon can ream a portion 42 of glenoid 40 (e.g., with a reaming tool and/or other drilling instrumentation) so as to be shaped to receive provisional augment 10. As shown, provisional augment 10 can be roughly cylindrical in shape. Thus, reamed portion 42 of glenoid 40 can have a cylindrical shape or profile to receive part or all of provisional augment 10. As illustrated, threaded insert 30 can be inserted into a hole bored in reamed portion 42 of glenoid 40, and then bottom surface 14 of provisional augment 10 can be placed against glenoid 40.

In some procedures, a surgeon can ream a defect of glenoid 40 in such a manner that more bone is removed from a particular area of glenoid 40 compared to other areas (e.g., eccentric reaming). Alternatively, a surgeon can ream glenoid 40 in a manner that would make glenoid 40 suitable for receiving an angled augment. Thus, in an example, the surgeon can choose a provisional augment 10 from a plurality of provisional augments 10 that form part of a kit, as detailed above, such that the selected provisional augment 10 is suitable for the particular patient. For instance, the surgeon might select a provisional augment that is angled in a posterior direction because a Walch B2 or B3 defect, which indicates a defect of posterior orientation, was repaired. In this instance, bottom surface 14 of provisional augment 10 can become seated within reamed portion 42 of glenoid 40, and top surface 12 of provisional augment 10 can be positioned in a substantially flat orientation. When situated on glenoid 40, projection 20 of provisional augment 10 can engage with threaded insert 30 so that provisional augment 10 is secured relative to glenoid 40. For instance, tabs 22 on projection 20 can be received in slots (not shown) on projection 32 of insert 30 so that provisional augment 10 is secured relative to glenoid 40. In an example, projection 20 can also be configured to secure to insert 30 through a threaded connection, press-fitting, or by another connection mechanism.

After attachment of provisional augment 10 and confirmation of the correct orientation thereof by the surgeon, the surgeon can then connect translator tool 50 to provisional augment 10, as shown in FIGS. 2-3. For instance, the surgeon can insert pins 58 into holes 16 of provisional augment 10, which can be substantially circular in shape, and pins 62 into holes 18, which can be formed as elongate slots. Since pins 58 can be fixed to body 60, and also substantially fixed laterally within holes 16 of provisional augment 10 (e.g., because the diameter of pins 58 can be substantially equal to the diameter of holes 16), pins 58 and body 60 can be rotationally stable or fixed relative to shaft 64 of translator tool 50. In other words, pins 58 and body 60 can be prevented from rotation about the longitudinal axis of shaft 64 of translator tool 50. At the same time, pins 62 can be connected to head 56 of translator tool 50, which is rotatable about the longitudinal axis of shaft 64 of tool 50 by way of handle 52. So, a surgeon can grasp handle 52 and rotate pins 62 within holes 18 of provisional augment 10 in either direction about the longitudinal axis of shaft 64 of translator tool 50. In this way, the surgeon can move pins 62 to a position that defines an appropriate screw trajectory and/or screw starting point for the ultimate augment that is intended for use with glenoid 40 (e.g., augment 120). Indeed, in an example, pins 62 can each extend along an axis that represents a screw trajectory and/or screw starting point through provisional augment 10 into glenoid 40. In this way, a surgeon can ensure that the screw trajectory and/or screw starting point is suitable for the operation at hand (e.g., the trajectory and/or starting point extends through suitable bone for the patient, and is positioned to provide maximum purchase for the ultimate augment that is implanted).

After a suitable screw trajectory and/or starting point is selected by way of pins 62, the surgeon can lock movement of pins 62 by rotating knob 66. Indeed, rotation of knob 66 can lock pins 62 about the longitudinal axis of shaft 64 of translator tool 50 by causing body 60 to move within the cavity of head 56, acting to compress head 56 between body 60 and shaft 64, as illustrated in FIG. 7 and described above. After the appropriate screw trajectory and/or starting point is selected and pins 62 are locked, the surgeon can remove translator tool 50 and provisional augment 10, if it remains attached to translator tool 50. Or, translator tool 50 could be removed first from provisional augment 10, and then provisional augment 10 could be removed from glenoid 40.

Referring to FIGS. 4A-B, before the above step or at the same time, baseplate 80 can be inserted onto alignment guide 100. In a particular example, center post 108 of alignment guide 100 can be inserted into bore 88 of post 86 of baseplate 80, and side posts 104 can be inserted into holes 84 of baseplate, as shown in FIG. 4B.

Then, translator tool 50 with pins 62 in the locked orientation can be detached from provisional augment 10 and attached to augment 120, as shown in FIGS. 5A-C. Since pins 62 can be locked when detaching translator tool 50 from provisional augment 10, pins 62 can retain their orientation as set by the surgeon in the step(s) above. As shown in FIGS. 5B-C, pins 62 can then be inserted into holes 128 of augment 120, and pins 58 can be inserted into holes 126 of augment 120. In this way, the proper screw trajectory and/or screw starting point as selected by the surgeon can be maintained.

Figure 6A:
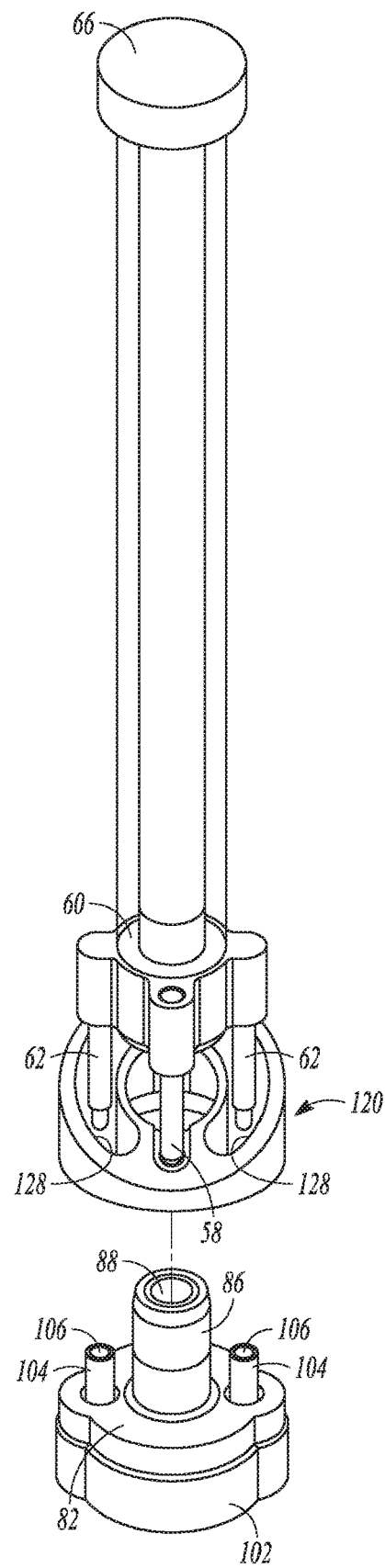
FIG. 6A is a perspective view of the translator tool and augment of FIGS. 5A-C being attached to the baseplate and alignment guide of FIGS. 4A-B.
Figure 6B:
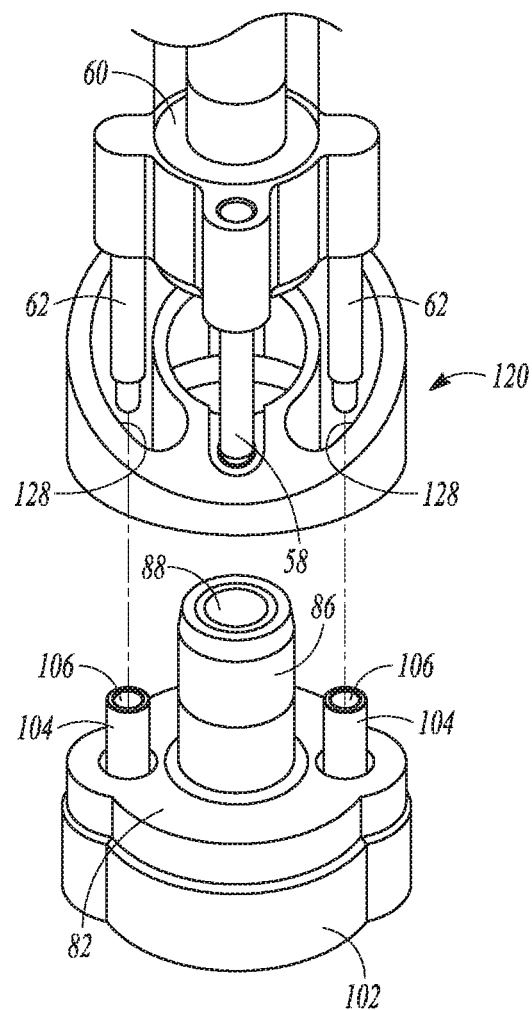
FIG. 6B is a close-up perspective view of FIG. 6A.
Figure 6C:
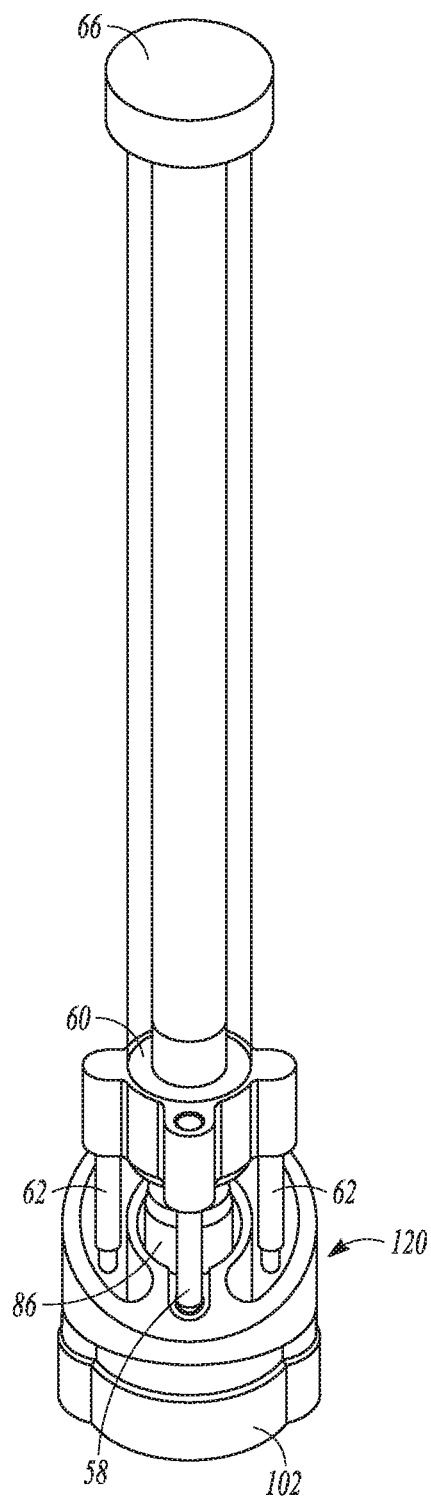
FIG. 6C is a perspective view of the translator tool and augment of FIGS. 5A-C fully connected to the baseplate and alignment guide of FIGS. 4A-B.

As shown in FIGS. 6A-C, with augment 120 attached to translator tool 50, the surgeon or another medical professional can attach augment 120 to the combination of baseplate 80 and alignment guide 100. In a particular example, post 86 of baseplate 80 can be configured as a Morse taper that is capable of interlocking with center opening 130 of augment 120 along a plurality of different orientations. Further, the orientation at which the post 86 of baseplate 80 locks to center opening 130 of augment 120 can dictate the screw trajectory and/or screw starting point for holes 84 of baseplate 80. Stated another way, post 86 of baseplate 80 is capable of being inserted into center opening 130 of augment 120 to establish a Morse-taper fit (e.g., a locking taper) therewith at a plurality of different angles. As such, with the augment 120 attached to translator tool 50 as shown in FIGS. 6A-C, pins 62 of translator tool 50 can be inserted into bores 106 of side posts 104 of alignment guide 100. Then, the surgeon or another professional can force translator tool 50 and augment 120 towards baseplate 80 (e.g., by tapping on knob 66 with a mallet) to cause pins 62 to move into side posts 104 and post 86 of baseplate 80 to lock within center opening 130 of augment 120 at the desired angulation. This can cause the selected screw trajectory and/or screw starting point of pins 62 to be maintained. As an example, since the surgeon is controlling the angle at which post 86 of baseplate 80 locks to center opening 130 of augment 120, the surgeon can ensure that the axes of holes 84 of baseplate 80 match or are aligned with the axes of pins 62. Also, the surgeon can control the correct rotational position of holes 84 of baseplate 80 relative to slots 128 of augment 120 so that an appropriate screw starting point is maintained.

Subsequently, the surgeon can remove translator tool 50 and alignment guide 100 from baseplate 80 and augment 120 so that baseplate 80 and augment 120 can be attached to glenoid 40. The surgeon can then engage bottom surface 124 of augment 120 to glenoid 40, and insert suitable bone screws through holes 84 of baseplate 80, through holes 128 of augment 120, and into glenoid 40. Since through the previous method the surgeon can set the trajectory and/or starting point of the axes of holes 84 of baseplate 80, insertion of screws into holes 84 can be along the exact trajectory and/or starting point selected by the surgeon as being the most appropriate for the surgical procedure at hand.

The surgeon can then attach other components useful for a shoulder replacement procedure (e.g., a rTSA procedure)

to baseplate 80, such as, for example, a glenosphere (not shown) or other intermediate components. Due to the preceding method, those components and/or baseplate 80 and augment 120 can be attached to glenoid 40 in a more secure fashion since an efficient screw trajectory and/or starting point can be selected by the surgeon and implemented to gain the maximum amount of purchase into bone. Thus, baseplate 80, augment 120, and/or any components attached thereto can be secured more efficiently to glenoid 40.

In the devices shown in the figures, particular structures are shown as being adapted for use in shoulder replacement procedures. The disclosure also contemplates the use of any alternative structures for such purposes, including structures having different lengths, shapes, and/or configurations. For example, although alignment guide 100 is used in the above procedure, it is contemplated that alignment guide 100 can be foregone in other alternate procedures. In this case, referring to FIGS. 6A-C, pins 62 of translator tool 50 might be inserted directly into openings 84 of baseplate 80 instead of into side posts 104 of an intermediate alignment guide 100. In addition, although a Morse taper is used for the interaction of post 86 of baseplate 80 and center opening 130 of augment 120, other connection mechanisms can be used that permit post 86 to be locked within opening 130 at various different angulations. For instance, a locking ball-and-socket arrangement can be used.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. An implant system comprising:
a tool having a shaft and a first projection;
a baseplate having a post and a first fastener aperture; and
an augment having a first opening configured to lockingly receive the post, wherein the first projection of the tool is insertable into the first fastener aperture of the baseplate and, when the first projection of the tool is inserted into the first fastener aperture, the first projection acts as a guide that directs the post of the baseplate into the first opening of the augment along a pre-defined trajectory, wherein the augment further comprises a second opening that is aligned with the first fastener aperture of the baseplate when the post of the baseplate is inserted into the first opening of the augment.

2. The implant system of claim 1, wherein the first projection is rotatable about a longitudinal axis of the shaft of the tool.

3. The implant system of claim 2, wherein the tool further comprises a second projection that is fixed about a longitudinal axis of the shaft of the tool.

4. The implant system of claim 1, wherein the post of the baseplate is lockable within the first opening of the augment along the pre-defined trajectory.

5. An implant system comprising:
a tool having a shaft and a first projection;
a baseplate having a post and a first fastener aperture;
an augment having a first opening configured to lockingly receive the post, wherein the first projection of the tool is insertable into the first fastener aperture of the baseplate and, when the first projection of the tool is inserted into the first fastener aperture, the first projection acts as a guide that directs the post of the baseplate into the first opening of the augment along a pre-defined trajectory; and
an alignment guide having a first projection that defines a first bore, wherein the first projection of the alignment guide is insertable into the first fastener aperture of the baseplate.

6. The implant system of claim 5, wherein the first projection of the tool is insertable into the first bore of the first projection of the alignment guide.

7. An implant system comprising:
a tool having a shaft and a first projection, wherein the tool further comprises a plurality of rotatable projections that are rotatable about a longitudinal axis of the tool, and a plurality of fixed projections that are fixed about the longitudinal axis;
a baseplate having a post and a first fastener aperture; and
an augment having a first opening configured to lockingly receive the post, wherein the first projection of the tool is insertable into the first fastener aperture of the baseplate and, when the first projection of the tool is inserted into the first fastener aperture, the first projection acts as a guide that directs the post of the baseplate into the first opening of the augment along a pre-defined trajectory, wherein the augment further comprises a plurality of first apertures configured to receive the plurality of fixed projections, and a plurality of elongate slots configured to receive the plurality of rotatable projections, and wherein each of the plurality of rotatable projections is movable laterally within an associated one of the plurality of elongate slots.

8. The implant system of claim 7, wherein each of the plurality of rotatable projections is lockable laterally within its associated elongate slot.

9. The implant system of claim 7, wherein the baseplate further comprises a plurality of fastener apertures configured to receive the plurality of rotatable projections.

10. The implant system of claim 9, wherein when the plurality of rotatable projections of the tool are received in the plurality of fastener apertures of the baseplate, the plurality of rotatable projections act as the guide that directs the post of the baseplate into the first opening of the augment along the pre-defined trajectory.

* * * * *